(12) United States Patent
Cheng et al.

(10) Patent No.: US 6,985,222 B2
(45) Date of Patent: Jan. 10, 2006

(54) CHAMBER LEAKAGE DETECTION BY MEASUREMENT OF REFLECTIVITY OF OXIDIZED THIN FILM

(75) Inventors: Hsi-Kuei Cheng, Hsin-Chu (TW); Chu-Chang Chen, Hsin-Chu (TW); Ting-Chun Wang, Hsin-Chu (TW); Szu-An Wu, Hsin-Chu (TW); Ying-Lang Wang, Hsin-Chu (TW); Hsien-Ping Feng, Hsin-Chu (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 375 days.

(21) Appl. No.: 10/423,379

(22) Filed: Apr. 25, 2003

(65) Prior Publication Data

US 2004/0212798 A1    Oct. 28, 2004

(51) Int. Cl.
*G01N 21/88* (2006.01)
(52) U.S. Cl. .................................. 356/240.1; 356/445
(58) Field of Classification Search ............. 356/240.1, 356/445–448, 630, 632, 503
See application file for complete search history.

(56) References Cited

U.S. PATENT DOCUMENTS

| | | | | |
|---|---|---|---|---|
| 3,869,211 A | * | 3/1975 | Watanabe et al. | ........... 356/632 |
| 3,892,490 A | * | 7/1975 | Uetsuki et al. | ............. 356/632 |
| 4,440,799 A | * | 4/1984 | Faith, Jr. | ...................... 438/18 |
| 4,484,818 A | * | 11/1984 | Houston | ..................... 356/445 |
| 4,828,391 A | * | 5/1989 | Zultzke et al. | .............. 356/632 |
| 5,414,506 A | * | 5/1995 | Saisho et al. | ............... 356/632 |
| 6,159,856 A | | 12/2000 | Nagano | |
| 6,197,646 B1 | | 3/2001 | Goto et al. | |
| 6,376,373 B1 | | 4/2002 | Nakamura et al. | |

OTHER PUBLICATIONS

Wolf, Stanley, Ph.D. and Tauber, Richard N., Ph., Silicon Processing for the VLSI Era, 2000; p. 104; vol. 1: Process Technology Second Edition: Lattice Press, Sunset Beach California, U.S.

* cited by examiner

*Primary Examiner*—Richard A. Rosenberger
(74) *Attorney, Agent, or Firm*—Slater & Matsil, L.L.P.

(57) ABSTRACT

A system and method for detecting chamber leakage by measuring the reflectivity of an oxidized thin film. In a preferred embodiment, a method of detecting leaks in a chamber includes providing a first monitor workpiece, placing the first monitor workpiece in the chamber, and forming at least one film on the first monitor workpiece. The reflectivity of the least one film of the first monitor workpiece is measured, wherein the reflectivity indicates whether there are leaks in the at least one seal of the chamber. In another embodiment, the method includes providing a second monitor workpiece, placing the second monitor workpiece in the chamber, and forming at least one film on the second monitor workpiece. The reflectivity of the at least one film of the second monitor workpiece is measured, and the second monitor workpiece film reflectivity is compared to the first monitor workpiece film reflectivity.

32 Claims, 5 Drawing Sheets

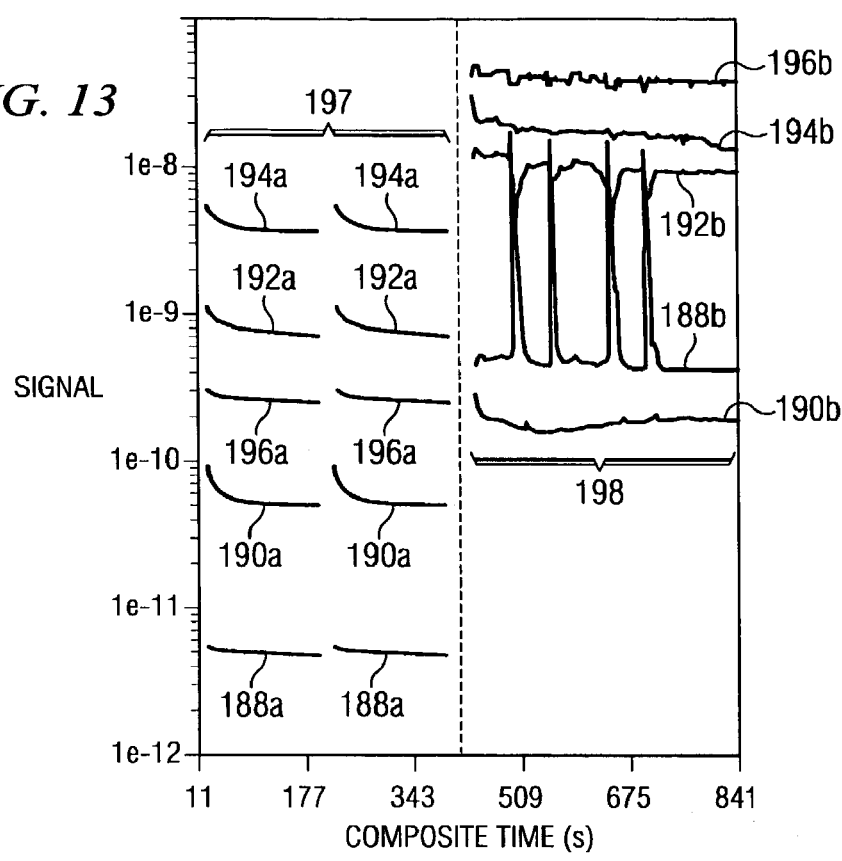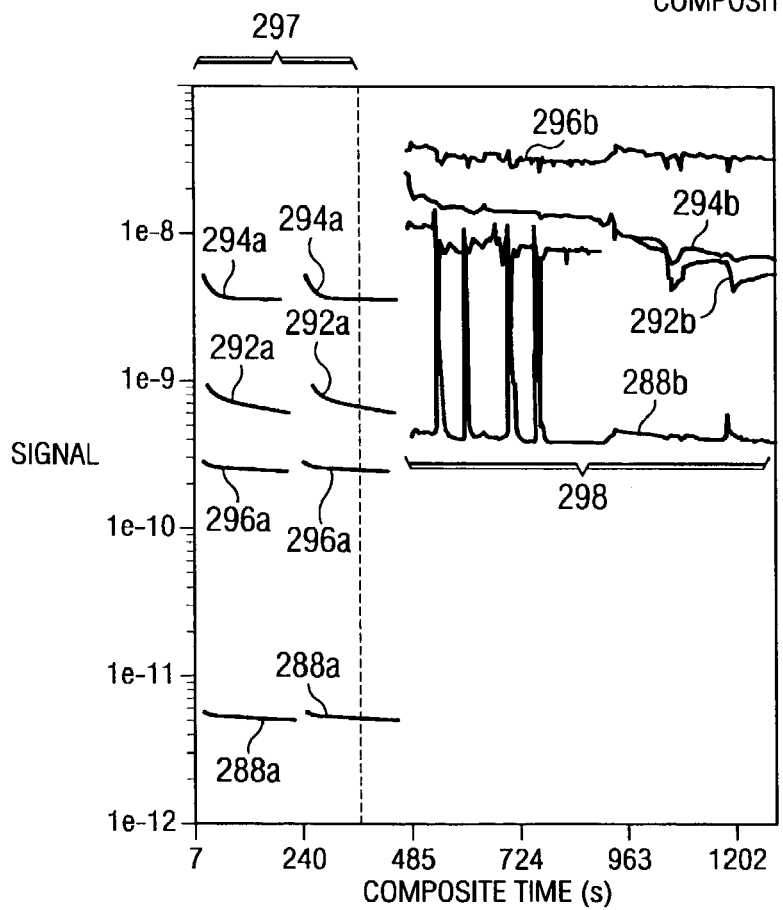

CHAMBER LEAKAGE DETECTION BY MEASUREMENT OF REFLECTIVITY OF OXIDIZED THIN FILM

TECHNICAL FIELD

The present invention relates generally to the fabrication of semiconductor devices, and more particularly to a system and method for detecting chamber leakage by measuring the reflectivity of an oxidized thin film.

BACKGROUND

Semiconductor devices are manufactured by depositing insulating, conductive, and semiconductive layers over a substrate or workpiece, and patterning the layers using photolithography to create integrated circuits. The layers deposited typically comprise thin films, which may be thermally grown or deposited from a vapor phase, for example. Thin films for use in very large scale integration (VLSI) and ultra-large scale integration (ULSI) fabrication must satisfy a large number of rigorous chemical, structural, and electrical requirements. Film composition and thickness must be strictly controlled to facilitate the etching of sub-micron features.

Rather complicated and expensive tools and systems are used to form thin films of a semiconductor wafer. The wafers may be handled by robots to avoid contamination by human interface, for example. The systems may be sealed, and may comprise many chambers that the wafers are moved in and out of for various processes. Leaks in a system can result in oxygen or water entering a chamber of the system, which can have detrimental effects to the thin film being formed, causing entire lots of wafers to be scrapped. Thus, what is needed in the art is a system and method of detecting chamber leakage in semiconductor device manufacturing systems.

SUMMARY OF THE INVENTION

These and other problems are generally solved or circumvented, and technical advantages are generally achieved, by preferred embodiments of the present invention, which comprises a system and method for detecting chamber leakage by measuring the reflectivity of a semiconductor monitor wafer surface.

In accordance with a preferred embodiment of the present invention, a method of detecting leaks in a chamber includes providing a first monitor workpiece and placing the first monitor workpiece in the chamber. The method includes forming at least one film on the first monitor workpiece, and measuring the reflectivity of the at least one film of the first monitor workpiece. The measured reflectivity indicates whether there are leaks in the at least one seal of the chamber.

In accordance with another preferred embodiment of the present invention, a method of detecting leaks in a processing chamber for semiconductor wafers includes providing a first monitor wafer, and placing the first monitor wafer in the processing chamber, the processing chamber including at least one seal, and having a plurality of sub-chambers. A first monitor film is formed over the first monitor wafer, and the first monitor wafer is passed through at least one sub-chamber of the processing chamber. A second monitor film is then formed over the first monitor film. The reflectivity of at least the second monitor film of the first monitor workpiece is measured, wherein the reflectivity indicates whether there are leaks in the at least one seal of the processing chamber.

In accordance with yet another preferred embodiment of the present invention, a system for processing semiconductor wafers includes a processing chamber, the processing chamber including at least one seal, the processing chamber including a mechanism for forming a film over a semiconductor wafer. The system includes a reflectivity measuring device for measuring the reflectivity of at least one film formed on a wafer in the processing chamber, and a processor adapted to analyze the reflectivity measured to determine whether there are leaks in the seal of the processing chamber.

Advantages of preferred embodiments of the present invention include providing the ability to detect leaks in a processing chamber, so that the leak may be repaired before running production lots of wafers, thus preventing poor film deposition and mass wafer scrap. Gas leakage in the processing chamber can be detected precisely, even under large amounts of pressure.

The foregoing has outlined rather broadly the features and technical advantages of embodiments of the present invention in order that the detailed description of the invention that follows may be better understood. Additional features and advantages of the invention will be described hereinafter, which form the subject of the claims of the invention. It should be appreciated by those skilled in the art that the conception and specific embodiments disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIG. 13 is a graph showing the reflectivity measurements comparing the results for a chamber having no leaks and a chamber having leaks at a pressure of $1.1 \times 10^{-6}$; and FIG. 14 is a graph showing the reflectivity measurements comparing the results for a chamber having no leaks and a chamber having leaks at a pressure of $9 \times 10^{-7}$.

Corresponding numerals and symbols in the different figures generally refer to corresponding parts unless otherwise indicated. The figures are drawn to clearly illustrate the relevant aspects of the preferred embodiments and are not necessarily drawn to scale.

DETAILED DESCRIPTION OF ILLUSTRATIVE EMBODIMENTS

The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

The present invention will be described with respect to preferred embodiments in a specific context, namely with respect to the manufacturing of semiconductor devices. The invention may also be applied, however, to other applications where thin films are formed on a surface.

Figure 1:
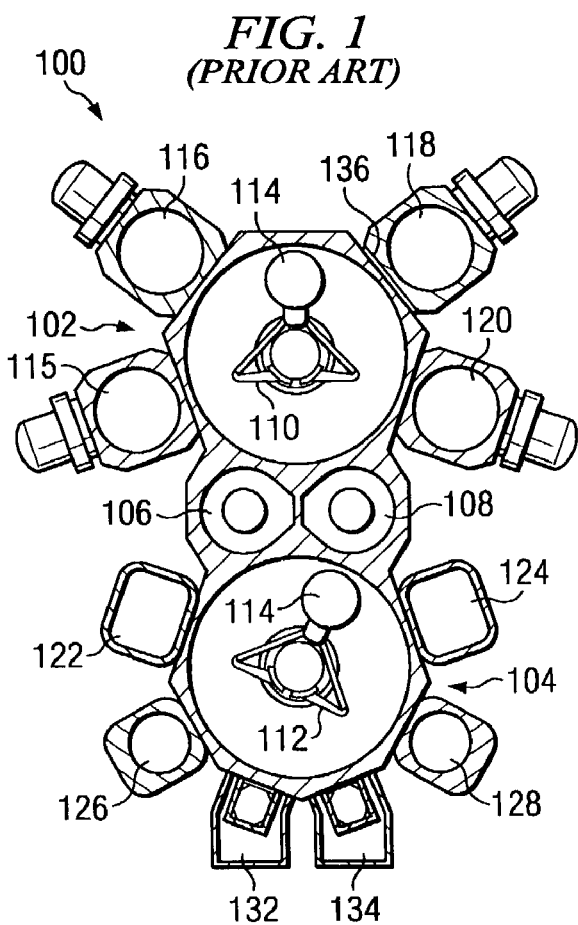
FIG. 1 illustrates a processing system for semiconductor wafers.

FIG. 1 shows illustrates a prior art processing system 100 for fabricating semiconductor wafers 114. The processing system 100, also referred to herein as a "processing chamber" or "chamber", comprises a first chamber 102 and a second chamber 104. The first chamber 102 may comprise a transfer chamber that is used to deposit cobalt and other materials on the wafers 114, for example. Cobalt is often deposited on semiconductor wafers 114 and annealed to form cobalt suicide over polysilicon regions of wafers 114, to lower the resistance of the polysilicon, for example. The second chamber 104 may comprise a buffer chamber, for example.

A pass-thru chamber 106 and a cool-down chamber 108 are coupled between the first and second chamber 102/104, as shown. The first chamber 102 is coupled to and/or may comprise a plurality of smaller processing chambers or sub-chambers 115, 116, 118 and 120. For example, chambers 115 and 116 may comprise chambers where cobalt (Co) is deposited by physical vapor deposition (PVD), for example, on the wafers 114. Chambers 118 and 120 may comprise chambers where titanium nitride (TiN) is deposited on the wafers 114, for example. The sub-chambers 115, 116, 118 and 120 may be adapted to form various materials by various deposition or formation methods on semiconductor wafers 114. Similarly, the second chamber 104 is coupled to a plurality of smaller processing chambers or sub-chambers 122, 124, 126, and 128. Chambers 122 and 124 may comprise pre-clean chambers, and chambers 126 and 128 may comprise orienter/degas chambers, as examples. Each processing sub-chamber 115, 116, 118, 120, 122, 124, 126, and 128 may be coupled to input and output tubes (not shown) that are adapted to transport various processing materials into and out of the chamber. The second chamber 104 may include a load lock 132/134, as shown.

A wafer handler 110 and 112 is located within each of the first and second chambers 102 and 104, respectively. The wafer handler 110/112 is adapted to move the wafers 114 to the appropriate sub-chambers and locations within the first and second chambers 102/104 while the wafers 114 are being processed. The wafers handlers 110/112 may be robotic and may be controllable by a computer program, or may be controllable by an operator, or both, for example.

To prevent the various gases and chemistries from entering and leaving the processing system 100, there are many seals 136 within the processing chamber 100. Only one seal 136 is shown between chamber 118 and transfer chamber 102, although the system 100 may include other seals at various locations. For example, there is a seal between the transfer chamber 102 and each processing sub-chamber 115, 116, 118 and 120. Similarly, there maybe a seal between the buffer chamber 104 and each processing sub-chamber 122, 124, 126, and 128. There are also seals between the load lock 132/134 and the second chamber 104, and between the pass-thru chamber 106, cool-down chamber 108 and the first and second chambers 102/104, as examples. The seal 136 shown may comprise a slit valve seal, for example. The processing system 100 may have other seals located around pipes or tubes, or within sidewalls of the various chambers and sub-chambers, for example (not shown).

A problem with the prior art processing system 100 is that these seals can leak, allowing $O_2$, $H_2O$, or other fluids to enter into the system 100. The requirements for thin film formation are stringent, and the introduction of even a small amount of $O_2$, $H_2O$, or other chemistries can result in an undesired film, such as an oxide, being deposited on the wafers 114. In particular, during the formation of certain types of thin films on wafers 114, seal leaks can result in entire lots of wafers 114 having to be scrapped.

Figure 2:
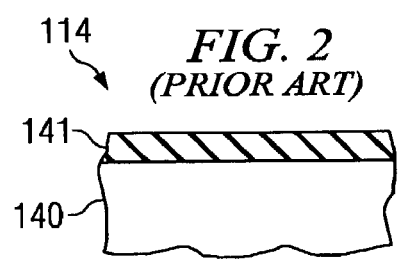
FIGS. 2 through 5 show cross-sectional views of a prior art semiconductor wafer in various stages of processing, wherein leaks in a processing chamber have resulted in undesired oxide growth.
Figure 3:
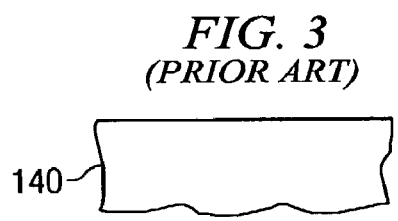

FIGS. 2 through 5 show cross-sectional views of a prior art semiconductor wafer in various stages of processing, wherein leaks in a processing chamber 100 such as the one shown in FIG. 1 have resulted in the formation of undesired oxide during a cobalt deposition. In FIG. 2, a cross-sectional view of a workpiece 140 which may include a semiconductor substrate, for example, is shown. The workpiece 140 may have one or more active regions formed in the substrate (not shown), and the workpiece 140 may have a native oxide 141 formed thereon. The wafer 114 is placed into the load lock 132/134 (not shown in FIG. 2; see FIG. 1) and the robotic wafer handler 112 moves the wafer to a cleaning chamber such as sub-chambers 122 or 124. The wafer 114 is cleaned, for example, using an argon (Ar) sputter, to remove the native oxide 141, as shown in FIG. 3.

Figure 4:
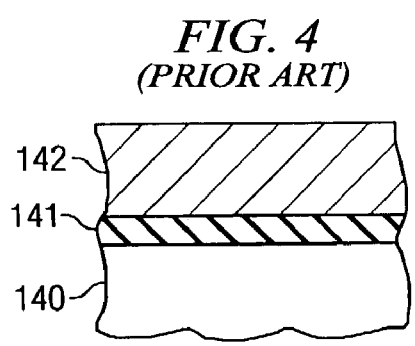

The wafer 114 is moved to the next processing sub-chamber, e.g., the wafer 114 may be moved through the pass-thru chamber 106 and to a deposition chamber such as 115 or 116. If there are leaks in the processing system 100, allowing $O_2$ or $H_2O$, as examples, to enter into the chambers 102/104, then a layer of silicon dioxide ($SiO_2$) 141 is formed on the surface of the wafer 114, due to the oxidation of the silicon substrate 140, as shown in FIG. 4. A layer of Co 142 is then deposited on the wafer 114, over the silicon dioxide 141.

Figure 5:
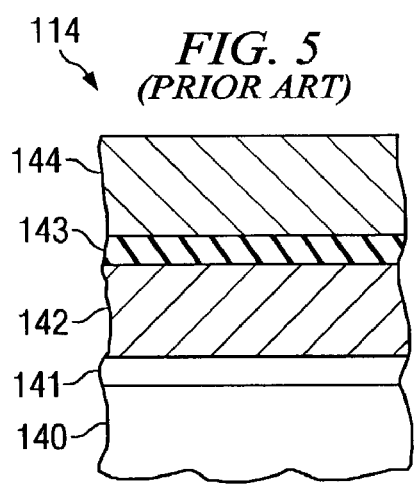

The wafer is moved by the robotic wafer handler 110 to a different deposition chamber such as sub-chamber 118 or 120. Again, if there are leaks in the processing system 100, allowing $O_2$ or $H_2O$, as examples, to enter into the chamber 102, then a thin layer of cobalt oxide ($Co_xO_y$) 143 is formed on the surface of the wafer 114 over the cobalt layer 142, due to the oxidation of the cobalt 142, as shown in FIG. 5. A layer of TiN 144 is then deposited over the wafer, over the cobalt oxide 143.

Figure 6:
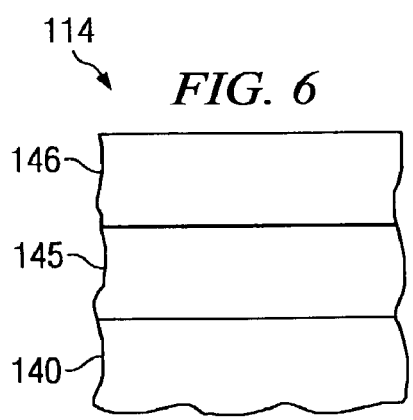
FIG. 6 shows an ideal case of the wafer shown in FIG. 5, without the oxide growth caused by processing chamber leaks.

FIG. 6 shows an ideal case of the wafer 114 shown in FIG. 5, without the undesired oxide growth caused by the processing chamber leaks. The wafer 114 shown in FIG. 6 was processed in a processing system 100 having no leaks, for example. After the Co 145 and TiN 146 are deposited on the workpiece 140, the wafer 114 may subsequently be annealed, during which silicon in the workpiece 140 reacts with the Co 145 to form $Co_xSi_y$ at the interface between the substrate 140 and the cobalt layer 145, for example (not shown). The residual unreacted cobalt 145 is then removed. The cobalt layer 145 may comprise a thickness of 500 Å or less, and the TiN layer 146 may comprise a thickness of 500 Å or less, as examples. This process to form a silicide is often used in the fabrication of metal oxide semiconductors (MOS), for example.

Figure 7:
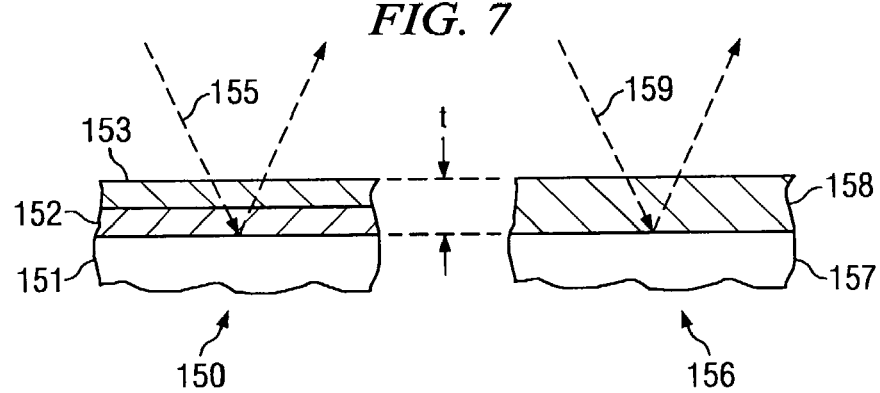
FIG. 7 illustrates cross-sectional views of semiconductor monitor wafers in accordance with an embodiment of the present invention, where there are no leaks in a processing chamber.

Referring again to FIG. 5, if undesired oxide layers such as $SiO_2$ layer 141 and $Co_xO_y$ layer 143 are formed due to leaks in the processing system 100, then this results in poor silicide $Co_xSi_y$ formation, because of the interfacial $SiO_2$ 141 and $Co_xO_y$ 143 films. Depending on the particular semiconductor device being fabricated, the $SiO_2$ 141 and $Co_xO_y$ 143 films may obstruct current, increase the resistance of the silicide, or disperse the wafer acceptance test (WAT) data. Often, the result is that the wafer 114 must be scrapped. Many times, leaks in a processing system 100 for semiconductor wafers are not found until after a large number of wafers 114 have been processed, resulting in entire lots of wafers 114 having to be scrapped. While leakage conditions can, in other applications, be measured by residue gas analysis (RGA), a RGA measurement device is costly and too large to assemble in a processing chamber Embodiments of the present invention achieve technical advantages as a system and method for detecting leaks in a chamber. Referring to FIG. 7, the method includes providing a first monitor workpiece 151, placing the first monitor workpiece 151 in a chamber 100 (e.g., such as the one shown in FIG. 1), and forming at least one film 152 on the first monitor workpiece 151, forming a first monitor wafer 150. The reflectivity of the least one film 152 of the first monitor workpiece 151 is measured, wherein the reflectivity indicates whether there are leaks in the at least one seal of the chamber. The reflectivity of the first monitor workpiece film 152 may be compared to the reflectivity of a film 158 deposited on a second monitor workpiece 157 (e.g., of second monitor wafer 156), or alternatively, to the reflectivity of a film deposited on a reference workpiece. The reflectivity comparison of the first and second monitor wafers 150 and 156 will reveal whether or not an oxide layer 154 (such as oxide layer 154; see FIG. 8) has been formed after the deposition of the first monitor workpiece film 152, indicating that the processing chamber 100 has a leak.

FIG. 7 illustrates cross-sectional views of a first monitor wafer 150 in accordance with an embodiment of the present invention, where there are no leaks in the processing chamber 100 (FIG. 1). A second monitor wafer 156, which may alternatively comprise a reference wafer, is also shown. The first monitor wafer 150 comprises a workpiece 151 which may comprise a semiconductor substrate, as an example. The first monitor wafer 150 is placed into the processing chamber 100 (such as the one shown in FIG. 1), and a first monitor film 152 is deposited over the workpiece 151. Preferably, the first monitor film 152 comprises a thin film that is pervious to light. The first monitor film 152 comprises a material that is subject to oxidation, and more preferably, comprises a conductor. The first monitor film 152 may comprise 20 to 50 Å of cobalt, deposited by PVD, as an example. Alternatively, the first monitor film 152 may comprise other materials and may be deposited by chemical vapor deposition (CVD) or other deposition techniques, as examples.

After a predetermined period of time, e.g., preferably about 5 minutes or more, and more preferably, long enough for an oxide layer to form over the first monitor film 152 if there is oxygen present within the processing chamber 100, a second monitor film 153 is deposited over the first monitor film 152. The second monitor film 153 preferably comprises the same material and thickness as the first monitor film 152, although alternatively, the second monitor film 153 may comprise other materials and thicknesses. Preferably, the second monitor film 153 comprises a material that is pervious to light.

The second monitor wafer 156 comprises a workpiece 157 having a third monitor film 158 deposited thereon. The third monitor film 158 preferably comprises a thickness "t" that is preferably equal to the thickness of the first monitor film 152 plus the thickness of the second monitor film 153. Preferably, also, the third monitor film 158 comprises the same material as the first and second monitor film 152/153 material.

The reflectivity of the surfaces of the first monitor wafer 150 and the second monitor wafer 156 is measured and compared. The reflectivity is measured using a measuring device, such as a reflectometer. The reflectivity may be measured on a relative scale using the reflectivity of silicon as a standard, with silicon having a reflectivity of "1", for example. Other measuring techniques may alternatively be implemented to measure the reflectivity, for example. The first monitor wafer 156 is preferably removed from the chamber 100, and the reflectivity of the first monitor wafer surface is measured while the wafer 156 is outside of the chamber.

As shown in FIG. 7, the first monitor wafer 150 is illuminated with light 155. Because first and second monitor layers 152 and 153 are pervious to light 155, the light 155 is reflected back from the workpiece 151 surface, and using optics reflection theory, the reflectivity is measured. Similarly, the second monitor wafer 156 is illuminated with light 159, and because the third monitor layer 158 is pervious to light, the light 159 is also reflected from the workpiece 157 surface. Because the thickness of the third monitor film 158 is approximately equal to the sum of the thicknesses of the first and second monitor films 152/153, the reflectivity measurements of the first and second monitor wafers 150 and 156 are approximately the same.

Figure 8:
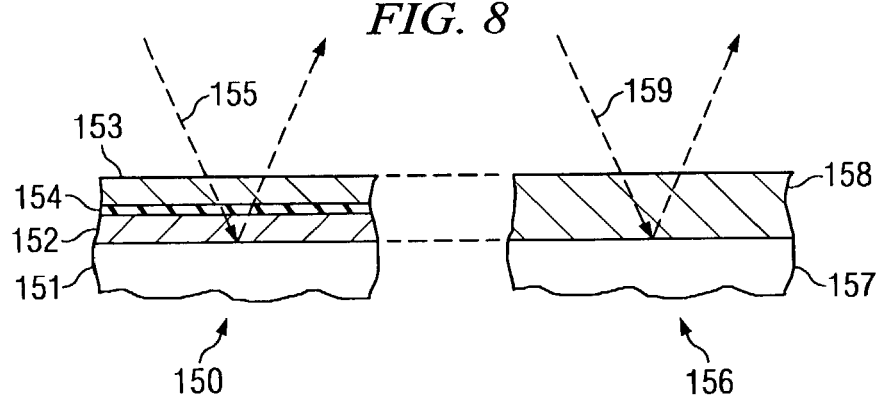
FIG. 8 illustrates cross-sectional views of semiconductor monitor wafers in accordance with an embodiment of the present invention, where there are leaks in a processing chamber.

However, in FIG. 8, the case is shown where a leak exists in the processing chamber 100, resulting in the formation of an oxide layer 154 over the first monitor layer 152. When the first monitor wafer 150 is illuminated with light, the light 155 is reflected back from the oxide layer 154 surface, so that the reflectivity of the first monitor wafer 150 is detectably different than the reflectivity of the second monitor wafer 156. Thus, the difference in the reflectivity of the first and second monitor wafers 150/156 surfaces indicates the presence of a leak in the processing chamber 100, in accordance with embodiments of the present invention.

Prior to the deposition of the second monitor film 153, the first monitor wafer 156 may be passed through at least one sub-chamber of the processing chamber (such as sub-chambers 115, 116, 118, 120, 122, 124, 126 or 128 shown in FIG. 1). If there is oxygen present in the sub-chamber that the first monitor wafer 156 is passed through, then an oxide layer 154 is formed over the first monitor film 152, as shown in FIG. 8. The leak within the sub-chamber is detectable by the measuring the reflectivity. Selected sub-chambers may be tested for leaks in this manner, to test a part of the processing system 100. Alternatively, the first monitor wafer 156 may be passed through all of the sub-chambers of the processing chamber, to test the entire processing chamber 100.

Figure 9:
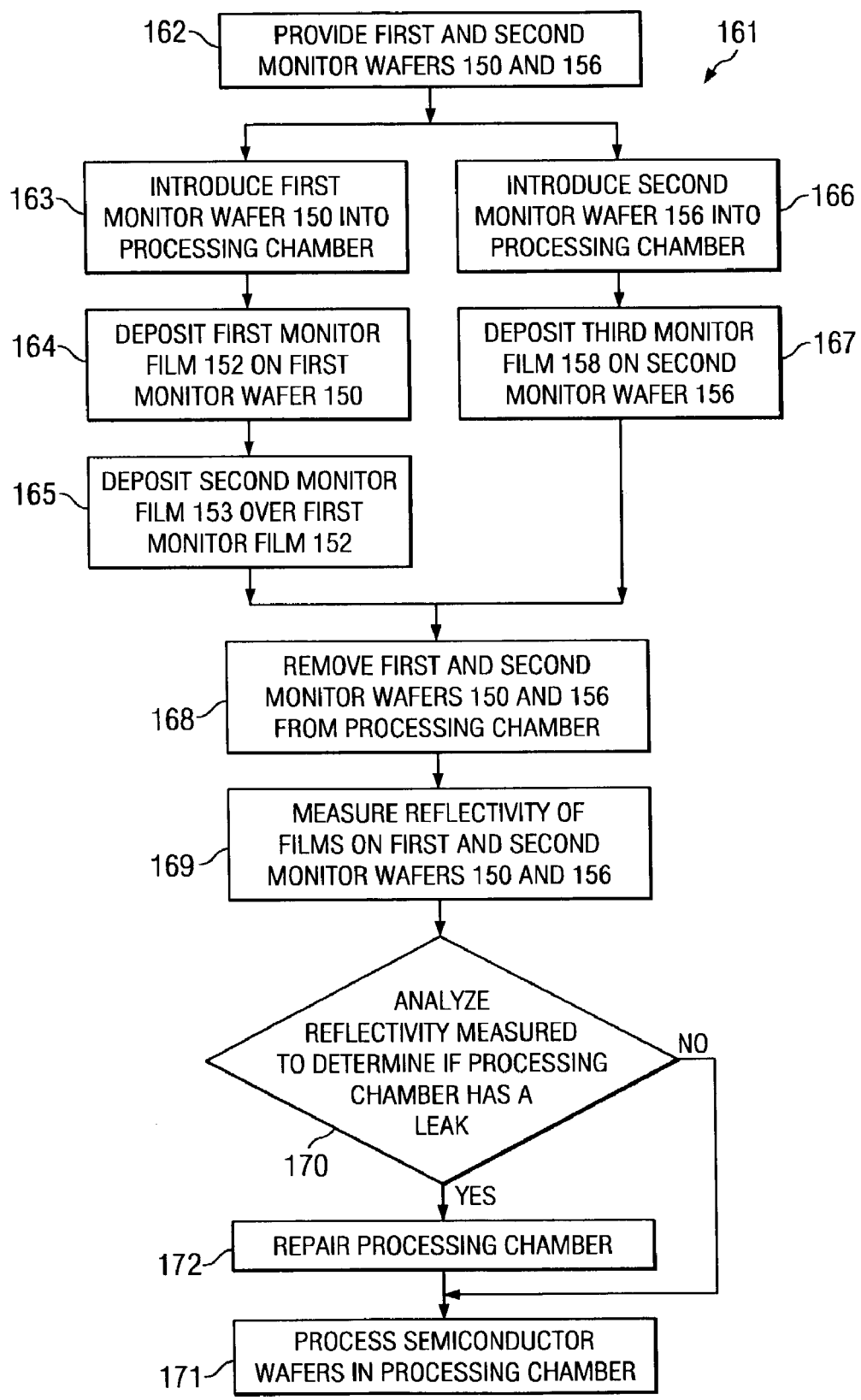
FIG. 9 is a flow chart of an embodiment of the invention.

FIG. 9 is a flow chart 161 for an embodiment of the invention. A first and second monitor wafer 150 and 156 are provided (step 162). The first monitor wafer 150 is placed into a processing chamber 100 (step 163). Optionally, the second monitor wafer 156 may be simultaneously placed into the processing chamber 100 (step 166). This is advantageous because the first and second monitor wafers 150/156 will be exposed to some of the same processing parameters, such as pressure and temperature, for example. Alternatively, the second monitor wafer 156 may be processed after or before the processing of the first monitor wafer 150, for example.

A first monitor film 152 is deposited on the first monitor wafer 150 (step 164). After a predetermined amount of time, and optionally, after the first monitor wafer 150 is passed through at least one of the sub-chambers of the processing chamber 100, a second monitor film 153 is deposited over the first monitor film 152 of the first monitor wafer 150 (step 165). A third monitor film 158 is deposited on the second monitor wafer 156 (step 167).

The first and second monitor wafers 150 and 156 may (optionally) then be removed from the processing chamber 100 (step 168). The reflectivity of the films on the surface of the first and second monitor wafers 150 and 156 is measured (step 169), and the reflectivity measured is analyzed to determine if the processing chamber has a leak (step 170). If a leak is detected, the leak in the processing chamber is repaired (step 172) before semiconductor wafers are processed in the processing chamber (step 171). If no leak is detected, then the processing chamber 100 is ready to process semiconductor wafers (step 171).

Figure 10:
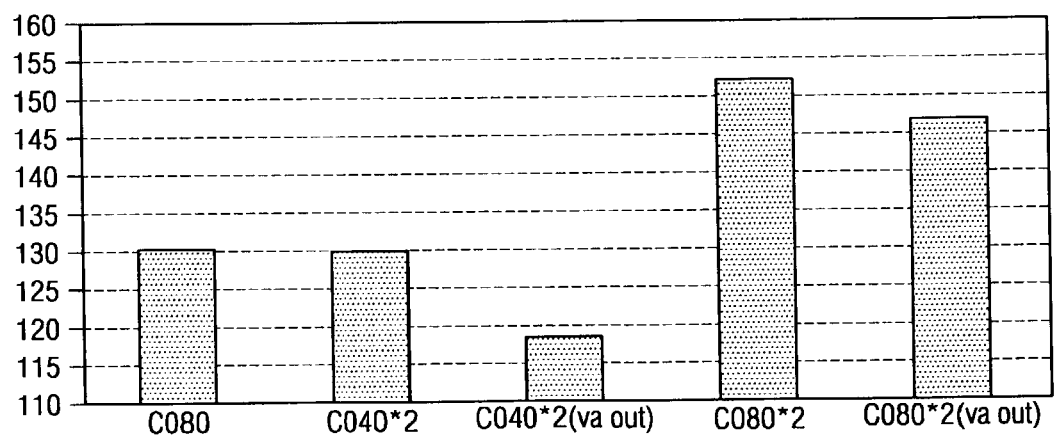
FIG. 10 is a chart showing the "vacuum out" measurement of various thicknesses of deposited cobalt films on monitor wafers.

FIG. 10 is a chart showing experimental results of the "vacuum out" measurement of various thicknesses of deposited cobalt films on monitor wafers. "CO80" indicates a measurement of the reflectivity of an 80 Å thick layer of third monitor film 158 on a second monitor wafer 156. The reflectivity measured was 130.25. "CO40*2" indicates a measurement of the reflectivity of two 40 Å thick layers of first and second monitor films 152 and 153 deposited on a first monitor wafer 150. With no oxygen present, and thus no oxide formed between the first and second monitor films 152 and 153, the reflectivity measured was 129.64, which is substantially the same as the CO80 reflectivity measurement.

However, "CO40*2 (va out)," indicates a measurement of the reflectivity of two 40 Å thick layers of first and second monitor films 152 and 153 deposited on a first monitor wafer 150, where oxygen (e.g., the absence of a vacuum allowed oxygen to enter the chamber) was present in the chamber after the first monitor film 152 deposition, resulting in the formation of an oxide between the first and second monitor films 152 and 153. The reflectivity measured for "CO40*2 (va out)" was 118.77, which is substantially different and detectable from the single 80 Å thick layer reflectivity measurement of 130.25. Thus, comparing the reflectivity results in the ability to detect a leak in the processing chamber.

"CO80*2" shows the reflectivity measurement for two layers of two 80 Å thick first and second monitor films 152 and 153 with no oxygen exposure, compared to two 80 Å thick layers with oxygen exposure, "CO80*2(va out)". Again, a difference in the reflectivity measured is detected.

Figure 11:
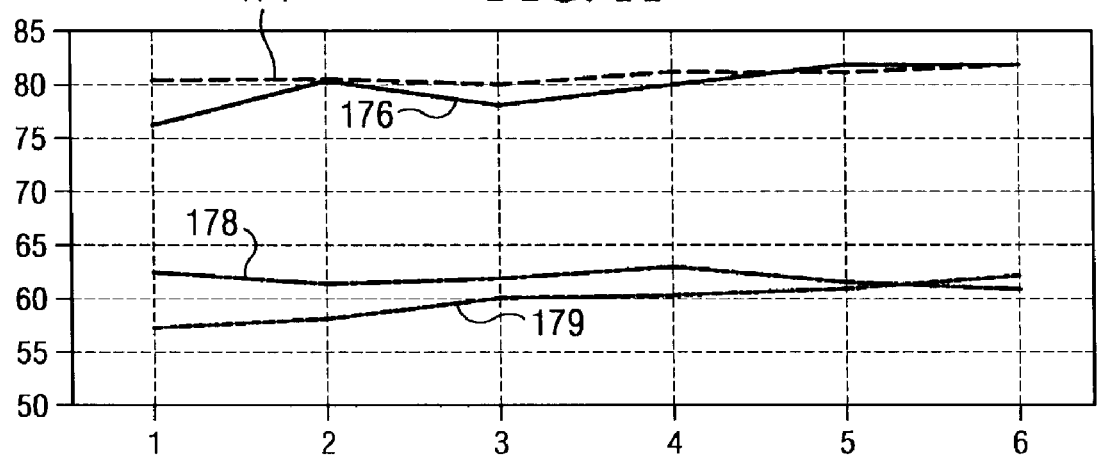
FIG. 11 is a graph illustrating a vacuum break monitor trend for various cobalt film thicknesses.

FIG. 11 is a graph illustrating a vacuum break monitor trend for various cobalt film thicknesses. A single 80 Å thick monitor film 158 of cobalt is indicated at 174, two 40 Å thick monitor films 152/153 of cobalt are indicated at 176, a single 60 Å thick monitor film 158 of cobalt is indicated at 178, and two 30 Å thick monitor films 152/153 of cobalt are indicated at 179. The graph illustrates the vacuum leak detected at various leakage conditions. For example, at higher pressure, more leakage tends to occur.

Figure 12:
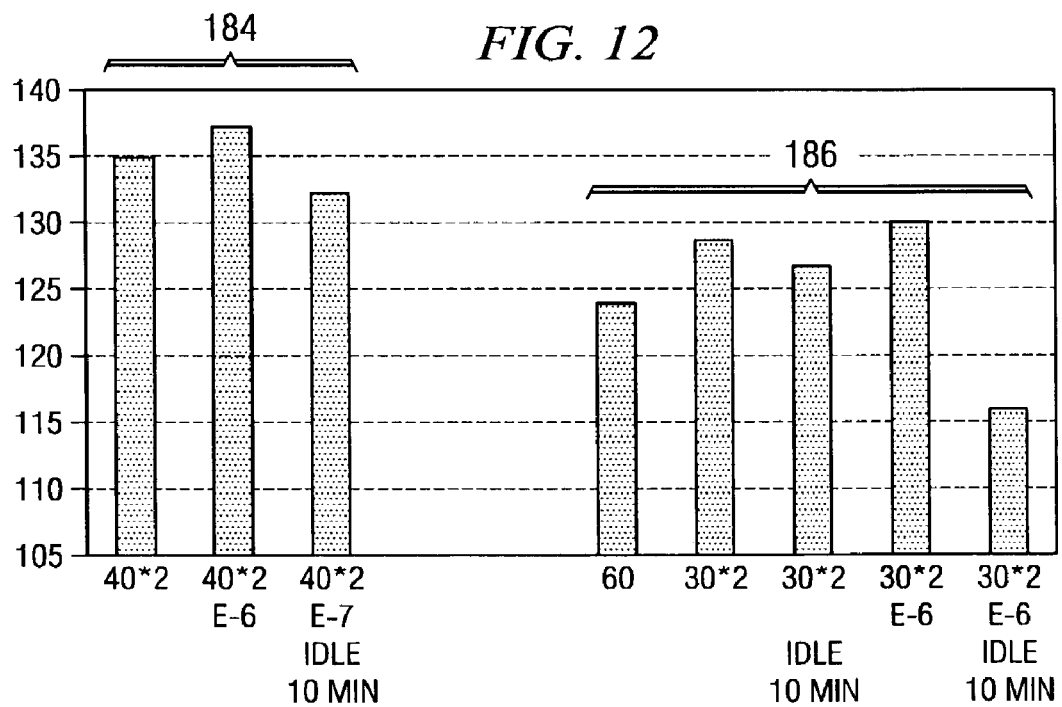
FIG. 12 is a chart showing the reflectivity measurements at two pressures for various thicknesses of cobalt films.

FIG. 12 is a chart shows the effect on the reflectivity measurements at various pressures for various thicknesses of cobalt films. Two layers of 40 Å thick first and second monitor films 152 and 153 are compared at 184, and one layer of 60 Å is compared to two layers of 30 Å thick first and second monitor films 152 and 153 at 186. Note that the film indicated at "40*2E-7 idle 10 min" (indicating a pressure of $9 \times 10^{-7}$) was idle 10 minutes in the processing chamber, during which an oxide formed, resulting in the decrease in reflectivity, when compared to the 40*2 graph. Similarly, the idle time and pressure varies the reflectivity results for the 60 and 30*2 Å results.

FIG. 13 is a graph showing the reflectivity measurements comparing the results for a chamber having no leaks and a chamber having leaks at a pressure of $1.1 \times 10^{-6}$. The Table 1 shows the element numbers of FIG. 13 and the chemistry each represents. The "a" side 197 of FIG. 13 indicates measurements for a chamber with no leakage, and the "b" side 198 of FIG. 13 indicates measurements for a chamber with leakage.

TABLE 1

| Element No. | Chemical |
| --- | --- |
| 188/288 | Ar |
| 190 | $CO_2$ |
| 192/292 | $O_2$ |
| 194/294 | $H_2O$ |
| 196/296 | $H_2$ |

FIG. 14 is a graph showing the reflectivity measurements comparing the results for a chamber having no leaks and a chamber having leaks at a pressure of $9 \times 10^{-7}$. Table 1 includes the element numbers of FIG. 14 and the chemistry each represents. The "a" side 297 of FIG. 13 indicates measurements for a chamber with no leakage, and the "b" side 298 of FIG. 13 indicates measurements for a chamber with leakage. Advantegeously, the experimental results indicated in FIGS. 13 and 14 show that at both pressures tested, (even at close to a vacuum, at $9 \times 10^{-7}$, in FIG. 14,) the method described herein can accurately detect leakage of the chamber.

Although embodiments of the present invention and its advantages have been described in detail, it should be understood that various changes, substitutions and alterations can be made herein without departing from the spirit and scope of the invention as defined by the appended claims. For example, many of the features and functions discussed above can be implemented in software, hardware, or firmware, or a combination thereof. As another example, it will be readily understood by those skilled in the art that the system and methods described herein may be varied while remaining within the scope of the present invention. While the system and method of detecting chamber leakage is described herein with reference to cobalt films and the formation of silicides, the system and method may also be used to detect chamber leakage relative to other films and materials. Embodiments of the present invention have application in the detection of gas leakage in any chamber.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of detecting leaks in a chamber, the chamber including at least one seal, the method comprising:
    providing a first monitor workpiece;
    placing the first monitor workpiece in the chamber and forming at least one film on the first monitor workpiece; and
    measuring the reflectivity of the at least one film of the first monitor workpiece, wherein the reflectivity indicates whether there are leaks in the at least one seal of the chamber.

2. The method according to claim 1, further comprising:
    providing a second monitor workpiece;
    placing the second monitor workpiece in the chamber;
    forming at least one film on the second monitor workpiece;
    measuring the reflectivity of the at least one film of the second monitor workpiece; and
    comparing the second monitor workpiece film reflectivity to the first monitor workpiece film reflectivity.

3. The method according to claim 2, wherein forming at least one film on the first monitor workpiece comprises forming a first monitor film over the first monitor workpiece and forming a second monitor film over the first monitor film, and wherein forming at least one film over the second monitor workpiece comprises forming a third monitor film over the second monitor workpiece.

4. The method according to claim 3, wherein the thickness of the third monitor film is approximately equal to the first monitor film thickness plus the second monitor film thickness.

5. The method according to claim 3, wherein the first, second and third monitor films comprise a metal.

6. The method according to claim 3, wherein the first, second and third monitor films comprise cobalt.

7. The method according to claim 3, wherein the chamber has a plurality of sub-chambers, further comprising, after forming the first monitor film over the first monitor workpiece, passing the first monitor workpiece through at least one of the sub-chambers of the chamber.

8. The method according to claim 7, wherein if the chamber has a leak, a fourth film is formed between the first and second monitor films of the first monitor workpiece, wherein the fourth film is detectable by the measured reflectivity of the first monitor workpiece.

9. The method according to claim 8, wherein the fourth film comprises an oxide.

10. The method according to claim 9, wherein the fourth film comprises cobalt oxide.

11. The method according to claim 3, wherein the first, second, and third monitor films are pervious to light.

12. The method according to claim 1, further comprising comparing the measured reflectivity to the reflectivity of a film on a reference workpiece.

13. A method of detecting leaks in a processing chamber for semiconductor wafers, comprising:
    providing a first monitor wafer;
    placing the first monitor wafer in the processing chamber, the processing chamber including at least one seal and having a plurality of sub-chambers;
    forming a first monitor film over the first monitor wafer;
    passing the first monitor wafer through at least one of the sub-chambers of the processing chamber;
    forming a second monitor film over the first monitor film; and
    measuring the reflectivity of at least the second monitor film of the first monitor workpiece, wherein the reflectivity indicates whether there are leaks in the at least one seal of the processing chamber.

14. The method according to claim 13, wherein the first and second monitor films are pervious to light.

15. The method according to claim 13, wherein the first and second monitor films comprise cobalt.

16. The method according to claim 13, wherein if the processing chamber has a leak, a fourth film is formed between the first and second monitor films of the first monitor wafer, wherein the fourth film is detectable by the measured reflectivity of the first monitor wafer.

17. The method according to claim 16, wherein the fourth film comprises an oxide.

18. The method according to claim 13, further comprising comparing the measured reflectivity to the reflectivity of a film on a reference wafer.

19. The method according to claim 13, further comprising removing the first monitor wafer from the processing chamber, before measuring the reflectivity.

20. The method according to claim 13, further comprising:
    providing a second monitor wafer;
    placing the second monitor wafer in the processing chamber;
    forming a third monitor film over the second monitor wafer, the third monitor film having a thickness approximately equal to the thickness of the first monitor film plus the second monitor film of the first monitor wafer;
    measuring the reflectivity of the third monitor film of the second monitor wafer; and
    comparing the second monitor wafer film reflectivity to the first monitor wafer film reflectivity.

21. The method according to claim 20, wherein the first, second and third monitor films are pervious to light.

22. The method according to claim 20, wherein the first, second and third monitor films comprise cobalt.

23. The method according to claim 20, wherein if the processing chamber has a leak, an oxide is formed between the first and second monitor films, wherein the oxide is detectable by comparing the second monitor wafer film reflectivity to the first monitor wafer film reflectivity.

24. The method according to claim 23, wherein the oxide comprises cobalt oxide.

25. The method according to claim 13, wherein passing the first monitor wafer through at least one of the sub-chambers comprises passing the first monitor wafer through all of the sub-chambers.

26. A system for processing semiconductor wafers, comprising:
    a processing chamber, the processing chamber including at least one seal, the processing chamber including a mechanism for forming a film over a semiconductor wafer;
    a reflectivity measuring device for measuring the reflectivity of at least one film formed on a wafer in the processing chamber; and a processor adapted to analyze the reflectivity measured to determine whether there are leaks in the seal of the processing chamber.

27. The system according to claim 26, wherein the processor is adapted to compare the measured reflectivity with the reflectivity of a reference wafer.

28. The system according to claim 26, wherein the wafer comprises a first monitor wafer, wherein the processor is adapted to compare the measured reflectivity of the first monitor wafer to a measured reflectivity of a film formed on a second monitor wafer.

29. The system according to claim 28, wherein the first monitor wafer has a first monitor film deposited thereon and a second monitor film deposited over the first monitor film, wherein the second monitor wafer comprises a third monitor film deposited thereon, wherein the processor is adapted to compare the reflectivity of at least the second monitor film of the first monitor wafer to the reflectivity of the third monitor film of the second monitor wafer.

30. The system according to claim 29, wherein if the processing chamber at least one seal has a leak, a fourth film is formed between the first monitor film and the second monitor film, wherein the fourth film changes the measured reflectivity of the first monitor wafer.

31. The system according to claim 30, wherein the fourth film comprises an oxide.

32. The system according to claim 29, wherein the first monitor film, second monitor film and third monitor film comprise cobalt.

* * * * *